United States Patent [19]

Cooper

[11] 4,129,281
[45] Dec. 12, 1978

[54] DOWEL RECEIVING CORE FOR CASTING DENTAL RESTORATIONS

[76] Inventor: Abraham J. Cooper, P.O. Box 321, Pomona, N.Y. 10970

[21] Appl. No.: 818,053

[22] Filed: Jul. 22, 1977

[51] Int. Cl.² .......................... A61C 13/12; B28B 1/14
[52] U.S. Cl. ..................... 249/54; 425/175; 32/11
[58] Field of Search .................. 249/54, 93; 425/175, 425/178, 179, 180; 32/11, 40 R; 269/254 R, 287, 234

[56] References Cited

U.S. PATENT DOCUMENTS

| 3,247,624 | 4/1966 | Denton | 269/287 X |
|---|---|---|---|
| 3,436,827 | 4/1969 | Dew | 32/11 |
| 3,553,839 | 1/1971 | Gores | 32/40 R X |
| 4,056,585 | 11/1977 | Waltke | 425/175 X |
| 4,060,899 | 12/1977 | Sauter | 32/11 |

*Primary Examiner*—Francis S. Husar
*Assistant Examiner*—John S. Brown
*Attorney, Agent, or Firm*—Albert F. Kronman

[57] ABSTRACT

Models for dental restoration work are provided with a plurality of elongated openings through which dowels secured to individual tooth members may be reached. The openings are formed by resilient cores cast in the models. The tooth members may thus be removed and replaced from the model easily and accurately. Two or more dowels may be used in each tooth member without need for careful spacing because of the slotted construction of the cores.

5 Claims, 6 Drawing Figures

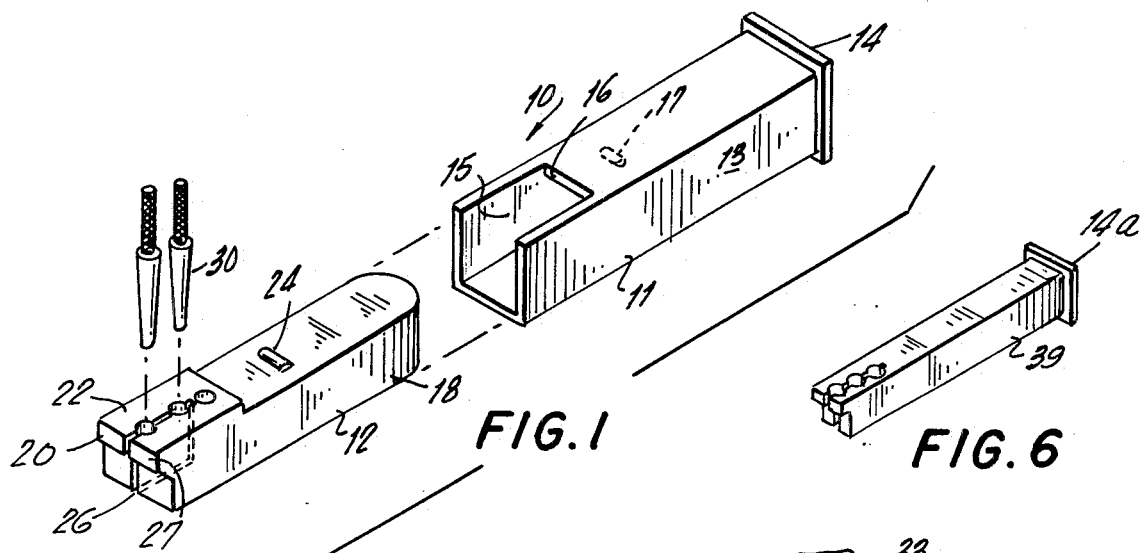
FIG. 1
FIG. 6
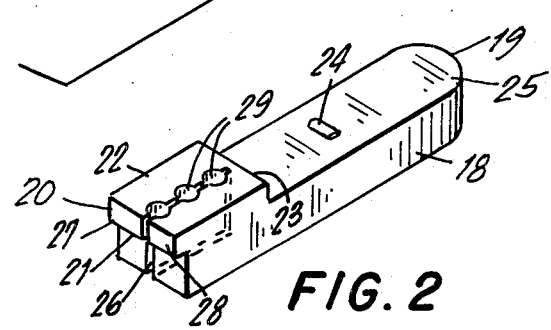
FIG. 2
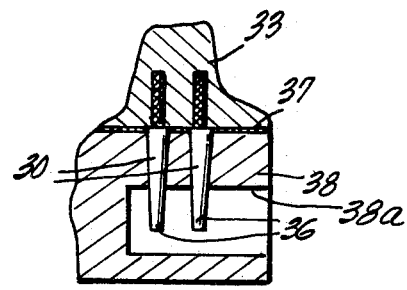
FIG. 5
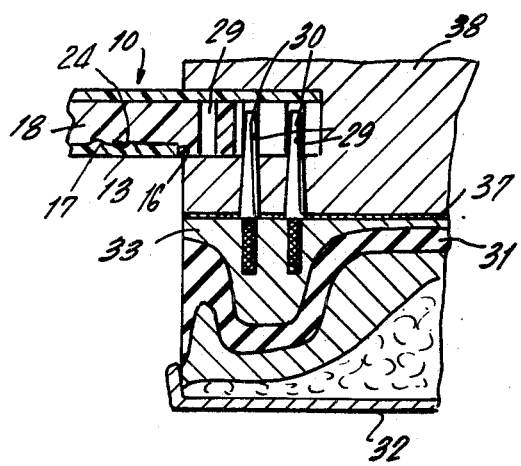
FIG. 4
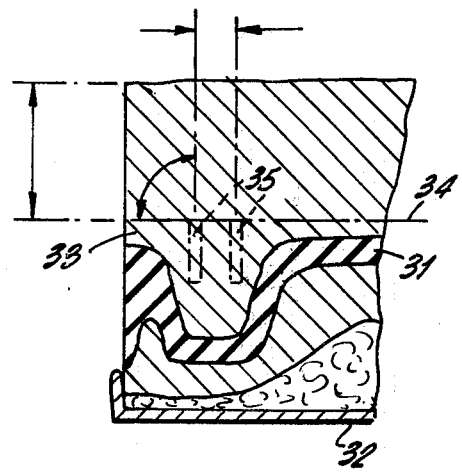
FIG. 3

DOWEL RECEIVING CORE FOR CASTING DENTAL RESTORATIONS

BACKGROUND OF THE INVENTION

It has been known in the casting of models for dental restoration work to employ brass dowels or pins secured to individual tooth members in the casting. After the casting is completed the individual tooth members are separated by cutting slots into the model between them. The tooth members are then individually removed from the model together with their attached dowels and worked on. Thereafter, they are replaced in the model using the dowels and the dowel receiving bores in the model to insure accurate positioning.

In order to remove individual tooth members from the model it is desirable to apply pressure to the free end of the dowels and thus force the tooth members free of the casting. U.S. Pat. No. 2,851,728 issued to Spaltan et. al. employed a wax plug placed within the wax box in contact with each of the dowels. The casting material was then poured around the plugs and after the casting hardened the wax was melted out leaving an elongated opening through which the dowels could be reached.

U.S. Pat. No. 3,286,350 issued to Cooper disclosed a two piece, pipe shaped core which was secured to the end of a dowel for each tooth in the casting and the casting material poured around it. This process eliminated the wax melting step.

In U.S. Pat. No. 3,461,562 issued to Cooper there was disclosed the use of a jig to support the cores and improve dowel alignment during casting of the model.

U.S. Pat. No. 3,871,804 issued to Cooper showed still another jig and means for placing two dowels in each tooth member to improve the accuracy of positioning.

In present day dental restoration work, it is often preferred to cast a model of the dental impression, grind the cast model down until it is substantially thin, and thereafter drill holes in the model to receive the dowel pins. The dowel pins are cemented into holes and additional casting material is poured around the dowel pins to form a base for the model. Employing this technique, it is still desirable to provide elongated openings in the model to reach the ends of the dowels so that individual tooth members can be ejected from the model.

Accordingly, it is an object of the present invention to provide core members which can be incorporated into the casting of a dental model to give access to the ends of the dowels after the casting has hardened, without the need for jigs.

Another object of the present invention is to provide core members which lend themselves to the use of two or more dowels in a single tooth member without the need for accurate spacing of the dowels.

A further object of the present invention is to provide a core structure which may be used for posterior as well as anterior teeth.

Still another object of the present invention is to provide a core structure which is easy to remove from the casting and which will maintain its position during casting operations without the need for special jigs.

SUMMARY OF THE INVENTION

In one embodiment of the present invention there is provided a two-piece core assembly made of some suitable resilient material consisting of an outer sleeve portion and an inner dowel retaining member. The dowel retaining member is telescopically received within the sleeve and is formed with a slot at its outer end having a plurality of spaced transverse bores therein. The bores are interconnected by an elongated slot which makes it possible to receive the ends of the dowels without regard to their spacing.

In another embodiment of the invention, the sleeved portion is omitted and the dowel receiving member is reduced in width to accomodate for use on anterior teeth which are small in size and closely spaced.

DESCRIPTION OF THE DRAWINGS

In the accompanying drawings forming part hereof, like members have been given identical reference numerals, in which drawings:

FIG. 1 is a somewhat isometric exploded view of one complete embodiment of the present invention.

FIG. 2 is a isometric view of the dowel receiving member shown in FIG. 1, slightly modified.

FIG. 3 is a view in vertical section of a casting poured into a dental impression in accordance with well known dental restoration techniques.

FIG. 4 is a view similar to FIG. 3 showing the manner in which the present invention is incorporated into the finished casting.

FIG. 5 is a fragmentary view of a portion of the finished casting in cross section showing a single tooth element.

FIG. 6 is a somewhat isometric view of a dowel receiving element made in accordance with the present invention and adapted to be used for anterior teeth.

General Description

Referring to the drawings and particularly FIGS. 1 and 2, 10 indicates a core assembly made in accordance with the present invention, consisting of a sleeve 11 and a dowel receiving member 12 slidable within the sleeve 11. The sleeve 11 consists of a body portion 13 in the form of a hollow elongated rectangulr shape. The body 13 is flanged at one end as shown at 14 in FIG. 1 and open at its opposite end 15 to accept the dowel receiving member 12. A stop recess 16 is formed in the upper wall of the body 13 and serves to limit the travel of the dowel receiving member 12 into the sleeve 11. A transverse boss 17, shown in dashed lines in FIG. 1, is molded on the upper interior surface of the sleeve 11 and serves to yieldably lock the dowel receiving member 12 in place, as hereinafter more fully described.

The dowel receiving member 12, as shown in FIGS. 1 and 2, consist of a body portion 18 of a shape which will freely slide within the sleeve 11. The body portion is preferably made of some resilient material such as vinyl which material is also suitable for the sleeve 11. One end of the body of 18 is rounded as indicated at 19 and the opposite, or dowel receiving, end 20 is stepped as shown at 21. The stepped portion 21 consists of a small platform like extension 22 having a rear bearing surface 23 which abuts the stop recess 16 in the sleeve 11 when the dowel receiving member has been inserted therein. At this juncture, a small rib 24 molded into the top surface 25 of the dowel receiving member 12 snaps under the boss 17 in the sleeve 11 to yiedably secure the sleeve and dowel receiving member together.

The platform extension 22 and the stepped portion of the dowel receiving member 12 are slotted as indicated at 26 to form spaced jaw members 27, 28 in the end of the dowel receiving member. In addition, a plurality of spaced bores 29 having a diameter somewhat smaller than that of the dowels 30 which are to be received therein, are provided along the longitudinal axis of the dowel receiving member slot 26. FIG. 1 shows the slot connecting all but one bore while the embodiment of FIG. 2 shows all the bores so connected.

Referring to FIG. 3, there is shown the manner in which a dental model is cast from an impression of the patient's mouth. This process is well known in the art and forms no part of the present invention. However, the nature of this process is felt to be important in understanding the present invention.

After the dentist makes an impression of the patient's mouth by means of some suitable plastic material inserted therein, it assumes a shape generally indicated at 31 which shape, corresponds to the gums and teeth of the patient. The impression 31 is placed upon a small tray 32 and a quantity of some casting material 33 such as plaster of paris or stone is poured into and over the impression 31. Thereafter, the cast material 33 is ground down to thin the amount of cast material to a suitable degree such as along the line 34. The thinned model is then placed beneath a drill or, in some instances on top of a drill. Small holes, indicated by the dashed lines 35 in FIG. 3, are drilled into the area represented by individual tooth members. As previously stated, it is preferred to put at least two such holes in each tooth member to prevent rotation of the teeth during the work of the technician in removing and replacing individual tooth members. The next step is to cement the dowels 30 into the holes 35 with some suitable cement material.

In practicing the present invention, the dowel receiving core members 10 are next slipped upon the ends of the dowels as indicated in FIG. 4. The configuration of the slot 26 and the bores 29 as well as the resilience of the material of which the dowel receiving member 12 is made, permit the said receiving member to grasp the ends of the dowels and extend outwardly as shown in FIG. 4. At this juncture some suitable parting material such as soap or other lubricant 37 well known in the art, is placed upon the upper surface of the cast material and around the dowels 30. An additional amount of cast material 38 is then poured over the assembly to provide a substantial base for the dental model as indicated in FIG. 4. When the cast material has hardened, the sleeves 11 can be pulled out of the cast material and thereafter the dowel receiving member 12 withdrawn from around the dowels 30. The resulting model has the appearance shown in FIG. 5 in which the ends 36 of the dowels 30 extend into the core cavity 38a so that, when the individual tooth members 38 are separated by sawing therebetween, pressure on the ends 36 of the dowels 30 will lift the tooth members free of the base 38 of the model.

The locking action of the boss 17 and rib 24 prevents accidental dislocation of the sleeve 11 and dowel receiving member 12 during casting operations and prevents casting materials from flowing therebetween which might prevent the core assembly from operating. In addition, the stop 16 and stepped portion 21 further serves to seal the space within the sleeve 11 during casting operations. The flange 14 around the open outer end of the sleeve 11 permits any casting material which may enter the sleeve to be removed and aids in sleeve removal.

Referring to FIG. 6 there is shown a further embodiment of the present invention which is useful in connection with anterior teeth. This embodiment is thinner than the dowel receiving member 12 so that the problem of small er teeth spaced closer together can be overcome. In this embodiment, the dowel receiving member 39 is used without a sleeve and the stepped portion 21 is not provided with a platform 22 for obvious reasons. In all other respects, the operation of the dowel receiving member 39 is similar to that of the first embodiment member 12. The end flange 14a aids in removing the dowel receiving member from the cast material.

Since the dowels are cemented in place before the remainder of the casting material is applied, they are accurately disposed normal to the surface of the model parallel to each other and firmly cemented in place so that there is no need to use jigs or other supporting devices for the core assemblies. The core assemblies remain firmly on the ends 36 of the dowels during the casting procedures. Since the dowels are parallel to each other, having been drilled from the same location, there is no difficulty in removing the tooth member with the dowels attached. This procedure eliminates the need for accurate alignment of the dowels which was time consuming and difficult in prior art processes.

Having thus fully described the invention what is desired to be claimed and secured by Letters Patent is:

1. A core assembly for use in casting models for dental restorations in which dowels are incorporated within the cast material beneath individual tooth members comprising a resilient sleeve having an elongated hollow body of rectangular cross-section, an elongated resilient dowel receiving member telescopically received within the sleeve; a longitudinal slot in the free end of the dowel receiving member, dividing the said dowel receiving member into spaced jaws, a plurality of transverse dowel receiving bores in the free end of the dowel receiving member extending parallel to the plane of the slot at least one of which is in communication with the said slot, and means carried by the sleeve and dowel receiving member to exclude casting material from the interior of the sleeve.

2. A core assembly according to claim 1 in which the sleeve is flanged at one end, open at its opposite end and provided with means to engage the dowel receiving member to yieldably secure it within the sleeve.

3. A core assembly according to claim 2 in which the securing means comprises a boss interiorly carried by the sleeve and a rib on the dowel receiving member engagable with said boss.

4. A core assembly according to claim 2 in which the sleeve is formed with a stop recess to receive a stepped portion on the free end of the dowel receiving member.

5. A core assembly according to claim 4 in which the longitudinal slot and bores extend through the stepped portion.

* * * * *